(12) United States Patent
Pigamo et al.

(10) Patent No.: US 9,567,274 B2
(45) Date of Patent: *Feb. 14, 2017

(54) PROCESS FOR THE MANUFACTURE OF 2-CHLORO-1,1,1,2-TETRAFLUOROPROPANE BY LIQUID PHASE FLUORINATION OF 2-CHLORO-3,3,3-TRIFLUOROPROPENE

(71) Applicant: Arkema France, Colombes (FR)

(72) Inventors: Anne Pigamo, Francheville (FR); Laurent Wendlinger, Soucieu En Jarrest (FR); Philippe Bonnet, Lyons (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/980,979

(22) Filed: Dec. 28, 2015

(65) Prior Publication Data

US 2016/0107957 A1    Apr. 21, 2016

Related U.S. Application Data

(63) Continuation of application No. 13/880,755, filed as application No. PCT/IB2010/003033 on Oct. 25, 2010, now Pat. No. 9,255,044.

(51) Int. Cl.
| | |
|---|---|
| *C07C 17/087* | (2006.01) |
| *C07C 17/383* | (2006.01) |
| *C07C 17/25* | (2006.01) |
| *C07C 17/38* | (2006.01) |
| *B01J 31/02* | (2006.01) |

(52) U.S. Cl.
CPC ............ *C07C 17/087* (2013.01); *C07C 17/25* (2013.01); *C07C 17/383* (2013.01); *B01J 31/0222* (2013.01); *B01J 31/0239* (2013.01); *B01J 31/0267* (2013.01); *B01J 31/0268* (2013.01); *B01J 2540/34* (2013.01); *B01J 2540/42* (2013.01); *B01J 2540/54* (2013.01); *C07C 17/38* (2013.01)

(58) Field of Classification Search
CPC ....... C07C 17/087; C07C 17/38; C07C 17/383
See application file for complete search history.

(56) References Cited

U.S. PATENT DOCUMENTS

| | | |
|---|---|---|
| 2004/0033892 A1 | 2/2004 | Bonnet et al. |
| 2009/0182179 A1 | 7/2009 | Merkel et al. |
| 2009/0240090 A1 | 9/2009 | Merkel et al. |
| 2009/0312585 A1 | 12/2009 | Merkel et al. |
| 2010/0036179 A1 * | 2/2010 | Merkel ............... C07C 17/087 570/156 |
| 2010/0191025 A1 | 7/2010 | Perdrieux |
| 2011/0031436 A1 | 2/2011 | Mahler et al. |

FOREIGN PATENT DOCUMENTS

| | | | |
|---|---|---|---|
| FR | WO 2008149011 A2 * | 12/2008 | ........... C07C 17/206 |
| WO | 2007079431 A2 | 7/2007 | |
| WO | 2008149011 A2 | 12/2008 | |

OTHER PUBLICATIONS

WO 2008149011 A2, Dec. 2008, pp. 1-4; English translation.*
Zhang, S. et al. J. Phys. Chem. Ref. Data 2006, 35, pp. 1475-1517.*

* cited by examiner

*Primary Examiner* — Jafar Parsa
*Assistant Examiner* — Medhanit Bahta
(74) *Attorney, Agent, or Firm* — Brinks Gilson & Lione

(57) ABSTRACT

Process of catalytic fluorination in liquid phase of product 2-chloro-3,3,3-trifluoropropene into product 2-chloro-1,1,1,2-tetrafluoropropane, with an ionic liquid based catalyst. Process for manufacturing 2,3,3,3-tetrafluoropropene.

13 Claims, No Drawings

PROCESS FOR THE MANUFACTURE OF 2-CHLORO-1,1,1,2-TETRAFLUOROPROPANE BY LIQUID PHASE FLUORINATION OF 2-CHLORO-3,3,3-TRIFLUOROPROPENE

CROSS-REFERENCE TO RELATED APPLICATIONS

This application is a Continuation of U.S. patent application Ser. No. 13/880,755 filed May 30, 2013, now allowed, which is a National Stage application of International Application No. PCT/IB2010/003033 filed Oct. 25, 2010.

FIELD OF THE INVENTION

The aim of the invention is the catalytic fluorination in liquid phase of product 2-chloro-3,3,3-trifluoropropene (HCFO 1233xf) into product 2-chloro-1,1,1,2-tetrafluoropropane (HCFO 244bb).

TECHNICAL BACKGROUND

The protocol of Montreal for the protection of the ozone layer led to the end of the use of chlorofluorocarbons (CFCs). Less aggressive compounds for the ozone layer, such as the hydrofluorocarbons (HFCs) e.g. HFC-134a replaced chlorofluorocarbons. These latter compounds were indeed shown to provide greenhouse gases. There exists a need for the development of technologies, which present a low ODP (ozone depletion potential) and a low GWP (global warming potential). Although the hydrofluorocarbons (HFCs), which are compounds which do not affect the ozone layer, were identified as interesting candidates, they exhibit a relatively high GWP value. There still exists the need to find compounds which exhibit a low GWP value. Hydrofluoroolefins (HFO) were identified as being possible alternatives with very low ODP and GWP values.

Several processes for production of HFOs compounds, in particular of propenes, were developed. The compound 244bb (2-chloro-1,1,1,2-tetrafluoropropane) is particularly desired as intermediate for the manufacture of 1234yf (2,3,3,3-tetrafluoropropene).

WO2007/079431 describes the synthesis of 244bb from 1233xf (2-chloro-3,3,3-trifluoropropene) either with liquid phase fluorination or gas phase fluorination. Liquid fluorination is disclosed with yields of 87-90%; however only overhead gases are considered, and the liquid phase remaining in the reactor is not analyzed.

US2009/0182179, US2009/0240090, US2009/0312585 and US2010/0036179 disclose the manufacture of 244bb starting from 1233xf. $SbCl_5$ is used as a catalyst in all these references. High selectivities are reported, such as up to 90%. Embodiments such as the addition of HCl in the liquid phase reactor or the use of a mixed catalyst $SbCl_3/SbCl_5$ are also disclosed.

WO2009/137658 illustrates the use of 1233xf as raw material for the production of 244bb in liquid phase fluorination. Yield into 244bb is indicated to be between 87 and 89%.

Selectivity is the key factor in the reaction. In fact, low conversion is acceptable if coupled with high selectivity, because it is easier to recycle unreacted feed than disposing by-products and reaction products that find no use in industrial processes, especially chlorinated products.

Thus, there is still a need for a process for the production of compound 244bb with a high selectivity.

SUMMARY OF THE INVENTION

The invention provides a process of catalytic fluorination in liquid phase of product 2-chloro-3,3,3-trifluoropropene (HCFO 1233xf) into product 2-chloro-1,1,1,2-tetrafluoropropane in presence of a catalyst.

Embodiments are the following:
the ionic liquid is obtained by reaction of at least one halogenated or oxyhalogenated Lewis acid based on aluminum, titanium, niobium, tantalum, tin, antimony, nickel, zinc or iron with a salt of general formula Y+A−, in which A− denotes a halide anion or hexafluoroantimonate anion and Y+ a quaternary ammonium cation, quaternary phosphonium cation or ternary sulfonium cation, preferably the catalyst is the fluorinated complex catalyst $emim^+Sb_2F_{11}^-$.

the process is carried out in a catalyst-rich phase, preferably with a molar ratio catalyst/organics higher than 50 mol %.

chlorine is added during the reaction, preferably according to a molar ratio from 0.05 to 20 mole %, preferably 1 to 17 mole % of chlorine per mole of starting compound.

a gas is injected, preferably an inert gas, more preferably nitrogen or helium. The flow of gas, compared to the flow of the starting product lies between 0.5:1 and 5:1, advantageously, between 1:1 and 3:1.

the product of the reaction is withdrawn in the gaseous state.

the temperature of the reaction ranges between 30° C. and 200° C., preferably between 40° C. and 170° C., advantageously between 50° C. and 150° C.

the pressure of the reaction is higher than 2 bar, preferably between 4 and 50 bar, in particular between 5 and 15 bar.

the molar ratio of HF:starting compound lies between 0.5:1 and 50:1, preferably between 3:1 with 20:1, advantageously between 5:1 and 15:1.

The process of the invention typically comprises the following steps:
(i) contacting 2-chloro-3,3,3-trifluoropropene with hydrogen fluoride in a liquid phase in the presence of an ionic liquid under conditions sufficient to form a reaction mixture comprising 2-chloro-1,1,1,2-tetrafluoropropane;
(ii) separating HCl and HF by a separation process from reaction mixture in order to form an organic mixture;
(iii) separating the organic mixture into a first stream comprising 2-chloro-1,1,1,2-tetrafluoropropane, and a second stream comprising unreacted 2-chloro-3,3,3-trifluoropropene;
(iv) recycling the unreacted 2-chloro-3,3,3-trifluoropropene to step (i).

Embodiments are the following:
step (ii): HCl is separated by distillation. HF can be separated by decantation or washing process.
step (iii) can be an extractive distillation step or a separation process using membranes. Alternatively, the organic mixture can be submitted to dehydrochlorination reaction in order to transform the 2-chloro-1,1,1,2-tetrafluoropropane into 1,1,1,2 tetrafluoro propene and then separate the resulting products from 2-chloro-3,3,3-trifluoropropene.

The process is preferably continuous.

The invention also provides a process for preparing 2,3,3,3-tetrafluoropropene, comprising the steps of:
(i) preparing 2-chloro-1,1,1,2-tetra fluoro propane by the process according to the first aspect of the invention;
(ii) dehydrochlorinating said *into* 2-chloro-1,1,1,2-tetrafluoropropane 2,3,3,3-tetra fluoropropene, preferably in a gas phase.

The invention relates to also the products obtained by following the steps of the process disclosed herewith, in particular a mixture containing mainly 244bb and impurities and/or unreacted starting materials and/or co-products.

DETAILED DESCRIPTION OF EMBODIMENTS

The invention is based on the positive impact of the liquid ionic based catalyst onto the selectivity in 244bb in the liquid-phase fluorination reaction of 1233xf. Selectivity is more important than conversion from an industrial point of view since non reactive product (due to low conversion) can be recycled but product that cannot be further transformed (due to low selectivity) is definitely lost.

The liquid ionic based catalyst is disclosed for example in patent applications WO2008/149011 (in particular from page 4, line 1 to page 6 line 15, included by reference) and WO01/81353 in the name of the applicant, as well as the reference "liquid-phase HF Fluorination", Multiphase Homogeneous Catalysis, Ed. Wiley-VCH, (2002), 535.

Suitable catalysts are derivatives of Lewis acids based on aluminum, titanium, niobium, tantalum, tin, antimony, nickel, zinc or iron. The ionic liquid is notably a non-aqueous salt having an ionic character that is liquid at moderate temperatures (preferably below 120° C.)

Ionic liquids based catalysts are preferably obtained by reaction of at least one halogenated or oxyhalogenated Lewis acid based on aluminum, titanium, niobium, tantalum, tin, antimony, nickel, zinc or iron with a salt of general formula Y+A−, in which A− denotes a halide (bromide, iodide and preferably chloride or fluoride) anion or hexafluoroantimonate (SbF6−) anion and Y+ a quaternary ammonium cation, quaternary phosphonium cation or ternary sulfonium cation.

Antimony based ionic liquids are preferred catalysts, like the reaction product of antimony pentachloride with ethyl-methyl-imidazolium chloride compound, providing fluorinated complex catalyst emim$^+$Sb$_2$F$_{11}^-$.

The reaction conditions (notably pressure) are such that the reactants are liquid. According to an embodiment the reactants are liquid while the reaction product is gaseous. The fact that the reaction products are gaseous allows their recovery in a gaseous phase at the exit of the reaction zone.

The temperature of the reaction may thus range between 30° C. and 200° C., preferably between 40° C. and 170° C., advantageously between 50° C. and 150° C.

The pressure of the reaction is typically higher than bar, preferably between 4 and 50 bar, in particular between 5 and 15 bar.

The molar ratio HF:starting compound lies generally between 0.5:1 and 50:1, preferably between 3:1 and 20:1, advantageously between 5:1 and 15:1.

The other reaction conditions, notably flow rates, can be determined by the skilled person according to common general knowledge, depending on the temperature, pressure, catalyst, reactant ratios, and the like. One shall take care to keep selectivity to the highest value.

A solvent can be used, albeit this is no the preferred embodiment. Such a solvent is an inert organic solvent under the reaction conditions. Such a solvent will be generally saturated, advantageously in C2 to C6, in order to avoid the reactions of addition. Such solvents can for example be those mentioned in patent application FR2733227. Such solvents have a boiling point (measured at atmospheric pressure), for example higher than 40° C., advantageously higher than 50° C., in particular higher than 60° C. Higher reaction temperatures will imply higher pressures, so that the boiling point of the solvent under the conditions of reaction is higher than the temperature of implementation of the reaction.

One can operate with variable ratios catalyst/organics, but in general one will prefer a catalyst-rich phase. For example, the molar ratio catalyst/organics is higher than 50 mol %. Preferably the starting medium is pure catalyst.

A chlorine stream may be used to increase the lifetime of the catalyst, typically in a quantity from 0.05 to 20 mole %, preferably 1 to 17 mole % of chlorine per mole of starting compound 1233xf. Chlorine may be introduced pure or mixed with an inert gas such as nitrogen or helium. The use of an ionic catalyst allows using small quantities of chlorine.

A raw material stabilizer may be used if necessary; typically in a quantity of 5-1000 ppm, preferably 10-500 ppm. This stabilizer can be for example p-methoxyphenol, t-amylphenol, thymol, limonene, d,l-limonene, quinones, hydroquinones, epoxides, amines and their mixtures.

It is also possible that the product of the reaction be stripped using a light gas allowing its drive by mechanical entrainment. Removing gaseous 244bb from the liquid phase reactor is advantageous (less side-reactions). The addition of a gaseous compound can be advantageous for the reaction, which can be favored for example by the improvement of agitation (bubbling).

This gas can be inert as the nitrogen or helium. The gas is preferably different from HCl.

The flow of gas, compared to the flow of the starting product lies typically between 0.5:1 and 5:1, advantageously, between 1:1 and 3:1.

The fluorination process in liquid phase according to the invention can be implemented continuously or semi-continuously. According to the preferred embodiment, the process is continuous.

The reactants (starting product and HF) and other compounds used in the reaction (chlorine, inert gas) can be fed in the reactor at the same place or at different places of the reactor. A preferred embodiment is when the gaseous compounds are injected in the bottom of the reactor, in particular in order to enhance the mechanical stripping and the mixing.

If a recycling is used, one can recycle directly at the inlet of the reactor or on a separate dip pipe.

The reaction is implemented in a reactor dedicated to the reactions involving halogens. Such reactors are known by the skilled worker and can comprise coatings containing Hastelloy®, Inconel®, Monel® or fluoropolymers. The reactor can be equipped with means for heat transfer.

Typically the process according to an embodiment of the invention is carried out as follows. The reactor (e.g. equipped with a catalyst stripping column) for the liquid phase reaction is loaded with ionic liquid based catalyst. Then 1233xf and HF are supplied continuously. A stream of anhydrous chlorine could also be injected, as well as an inert gas.

The stream which is withdrawn from the reaction zone is in a gaseous form and mainly comprises 244bb, as well as isomers of the 240 series (241+242+243), and chlorine and inert gas, together with unreacted 1233xf and HF.

244bb is separated from this stream while other products (1233xf HF and 240 series isomers) are recycled to the reactor.

The 244bb that is produced according to the invention is used to manufacture 1234yf. Manufacture of 1234yf starting from 244bb is known and uses a dehydrochlorination catalyst. The reaction is preferably carried out in gas phase, as is known in the art. The dehydrochlorination catalyst may be metal halides, halogenated metal oxides, neutral (or zero oxidation state) metal or metal alloy, or activated carbon in bulk or supported form.

One may revert to the following patent applications, incorporated herein by reference, US2009/0182179, US2009/0240090, US2009/0312585 and US2010/0036179, for a disclosure of the reaction 244bb into 1234yf. This reaction is known to the skilled man.

EXAMPLES

The following examples illustrate the invention without limiting it.

The equipment used consists of a jacketed autoclave of a capacity of 1 liter, made of stainless steel 316L, which is stirred using a magnetic stirrer. It is equipped with pressure and temperature indicators. Apertures on the head of the autoclave allow introducing the reactants and degasification. It comprises at the top a condenser as well as a valve for regulating the pressure. The condenser is controlled in temperature using an independent thermostated bath.

The products of the reaction are extracted continuously during the reaction. They enter a scrubber which collects hydracids HF and HCl and then are cold trapped in liquid nitrogen. The increase of weight of the scrubber and of the trap makes it possible to establish a mass balance.

At the end of the period of reaction, the reaction medium is degassed in order to evacuate residual HF. For this period of degasification, the organics possibly drawn are also trapped, always after having crossed the scrubber which makes it possible to eliminate HF and HCl from the gas flow. In a last stage, the autoclave is opened and drained, a sample of the organic phase is analyzed after having hydrolyzed and extracted the catalyst with a hydrochloric acid solution.

The analysis is made then by gas phase chromatography on a sample of expanded liquid. The analysis by chromatography is carried out using a column CP Sil 8, dimensions 50 m*0.32 mm*5 µm. The programming of temperature of the furnace is the following one: 40° C. during 10 min then slope of 4° C./min until 200° C.

Considering that xi is the initial amount of moles of raw material and xf the total final amount of moles of raw material, conversion (%) is: (xi−xf)/xi*100. Selectivity of a product is calculated by the ratio between the amount of moles recovered of this product and the total amount of moles of products of reaction.

Example 1

Comparative 150 ml of $SbCl_5$, catalyst is introduced in the reactor and fluorinated with flowing anhydrous HF at 60° C. during two hours. The flow of HF is added according a molar ratio of 5:1 respect to the catalyst amount. Chlorine is also added continuously to maintain a high level of oxidation of antimony. The flow of chlorine is kept at 1 g/h for the prefluorination step and all along the experiment. (15% during conversion step).

After this prefluorination step, 0.5 moles of 1233xf are introduced in the reactor. The temperature is adjusted at 85° C. Anhydrous HF is flowing with a rate of 1 mole/h during the 5 hours of the experiment. The pressure is 8 bar. The condenser set-point is 90° C. (meaning there is no reflux into the reactor). Helium is flowing through a deep tube of the reactor with a flow rate of 3.4 Nl/h. (ratio of 1.5).

After 5 hours, pressure is released and the reactor is heated to remove residual HF. When opening, 289 g of catalyst are remaining at the bottom of the reactor. Organics reactant and product have been collected in the cold trap during the experiment. Results in terms of conversion and selectivity are given on the table 1.

Example 2

Invention 100 ml of $SbCl_5$, and 50 ml of ethyl-methyl-imidazolium chloride compound, providing fluorinated complex catalyst $emim^+Sb_2F_{11}^-$, are introduced in the reactor and fluorinated with flowing anhydrous HF at 60° C. during two hours. The flow of HF is added according a molar ratio of 5:1 respect to the catalyst amount. Chlorine is also added continuously to maintain a high level of oxidation of antimony. The flow of chlorine is kept at 1 g/h for the prefluorination step and all along the experiment.

The conditions of example 1 are then applied. Results are given in table 1.

TABLE 1

|  | Example 1 | Example 2 |
|---|---|---|
| Catalyst | SbCl5 | SbCl5 + emimCl |
| Mass balance (%) | 97.3 | 98.4 |
| Conversion (%) | 75.3 | 16.7 |
| Selectivities (%) | | |
| 245cb | 0.2 | 0.2 |
| 244bb | 76.3 | 92.6 |
| 1223xd | 1.3 | 0.06 |
| 1232xf | 3.9 | 0.03 |
| 233ab | 4.5 | 0.5 |
| 241 + 242 + 243 isomers | 4.7 | 4.0 |
| Unknown | 9.1 | 2.6 |

One will notice that unknown compounds represent a signification amount in the comparative example while it is at a low level for the invention (9.1 v. 2.6). Also, 1223xd ($CF_3$-CCl=CHCl) and 233ab($CF_3$-CCl2-CHCl) are chlorinated by-products and are formed in high amounts in the comparative example while it is at a low level for the invention (1.3+4.5=5.8 v. 0.06+0.5=0.56). For the unwanted side-products, the comparative example will produce 14.9% while for the invention this is below 3.2, hence about 12% difference, which is very significant. The selectivity for the invention is thus very high, making recycling possible and easy.

The invention claimed is:

1. A process for producing 2-chloro-1,1,1,2-tetrafluoropropane comprising:
   (i) reacting 2-chloro-3,3,3-trifluoropropene with hydrogen fluoride in the presence of an ionic liquid based catalyst under conditions sufficient to form a reaction mixture comprising 2-chloro-1,1,1,2-tetrafluoropropane and HCl as a byproduct, wherein the catalys is obtained by reacting at least one halogenated or oxyhalogenated Lewis acid based on aluminum, titanium, niobium, tantalum, tin, antimony, nickel, zinc or iron with a salt of general formula Y+A−, in which A− denotes a halide anion or hexafluoroantimonate anion and Y+ a quaternary ammonium cation, quaternary phosphonium cation or ternary sulfonium cation;

(ii) separating HCl and HF by a separation process from the reaction mixture to form an organic mixture;

(iii) separating said organic mixture into a first stream comprising 2-chloro-1,1,1,2-tetrafluoropropane, and a second stream comprising unreacted 2-chloro-3,3,3-trifluoropropene; and (iv) recycling the unreacted 2-chloro-3,3,3-trifluoropropene to step (i).

2. The process according to claim 1, wherein the catalyst is the fluorinated complex catalyst emim$^+$Sb$_2$F$_{11}^-$.

3. The process according to claim 1, carried out in a catalyst-rich phase.

4. The process according to claim 1, in which chlorine is added during the reaction.

5. The process according to claim 1, wherein a gas is injected during step (i).

6. The process according to claim 5, in which the flow of gas, compared to the flow of the starting product lies between 0.5:1 and 5:1.

7. The process according to claim 1, in which the product of the reaction is withdrawn in the gaseous state.

8. The process according to claim 1, in which the temperature of the reaction ranges between 30° C. and 200° C.

9. The process according to claim 1, in which the pressure of the reaction is higher than 2 bar.

10. The process according to claim 1, in which the molar ratio of HF: starting compound lies between 0.5:1 and 50:1.

11. The process according to claim 1, which is continuous.

12. A process for preparing 2,3,3,3-tetrafluoropropene, comprising:

(i) preparing 2-chloro-1,1,1,2-tetra fluoro propane by the process according to claim 1; and then (ii) dehydrochlorinating said 2-chloro-1,1,1,2-tetrafluoropropane into 2,3,3,3-tetra fluoropropene.

13. The process according to claim 12, wherein the dehydrochlorination is performed in a gas phase.

* * * * *